United States Patent [19]

Kopp et al.

[11] Patent Number: 5,100,998
[45] Date of Patent: Mar. 31, 1992

[54] PROCESS FOR IMPROVING THE FLOWABILITY OF DIMERIZED 2,4-TOLYLENEDIISOCYANATE

[75] Inventors: Richard Kopp, Cologne; Gerhard Grögler, Leverkusen; Heinrich Hess, Cologne; Lutz Georgias, Dormagen; Helmut Hurnik, Leverkusen; Hans D. Thomas, Bergisch Gladbach, all of Fed. Rep. of Germany

[73] Assignee: Bayer Aktiengesellschaft, Leverkusen Bayerwerk, Fed. Rep. of Germany

[21] Appl. No.: 638,879

[22] Filed: Jan. 8, 1991

[30] Foreign Application Priority Data

Jan. 18, 1990 [DE] Fed. Rep. of Germany ....... 4001247

[51] Int. Cl.$^5$ .............................................. C08G 18/78
[52] U.S. Cl. ................... 528/73; 252/182.2; 540/202; 106/287.34
[58] Field of Search ............. 528/73; 252/182.2; 540/202; 106/287.34

[56] References Cited

U.S. PATENT DOCUMENTS 3,223,584 12/1965 Luckenbaugh et al. ............ 540/202

FOREIGN PATENT DOCUMENTS 308710 3/1989 European Pat. Off. .

Primary Examiner—Maurice J. Welsh
Assistant Examiner—Rachel Johnson
Attorney, Agent, or Firm—Joseph C. Gil; Godfried R. Akorli

[57] ABSTRACT

The invention relates to a process for improving the flowability and preventing the agglomeration of finely divided dimerized 2,4-toluene diisocyanate in which a precipitated silicas and/or pyrogenic silica having a hydrophobic surface is added to the finely divided dimerized 2,4-toluene diisocyanate. The invention also relates to the finely divided dimerized 2,4-toluene diisocyanate prepared by this process.

11 Claims, No Drawings

PROCESS FOR IMPROVING THE FLOWABILITY OF DIMERIZED 2,4-TOLYLENEDIISOCYANATE

BACKGROUND OF THE INVENTION

This invention relates to a process for improving the flowability and preventing the agglomeration of finely ground dimerized 2,4-toluene diisocyanate by the addition of precipitated silicas and/or pyrogenic silicas having a hydrophobic surface.

At present, the only solid, relatively high melting diisocyanate that is available on the market is finely ground dimerized 2,4-toluene diisocyanate (trade product DESMODUR ®TT of Bayer AG, West Germany)

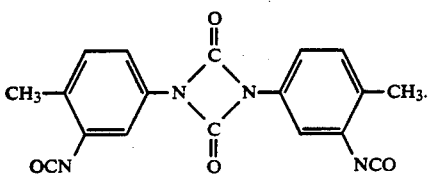

(I)

This material is used mainly in PVC primers and for the production of polyurethane rubber, where it is used for obtaining a homogeneous end product in a very fine form. A more recent field of application is use in polyurethane one-component systems based on solid polyisocyanates.

The commercial DESMODUR ® TT product is in the form of a white powder having a particle size of from 2 to 25 μm. In transport and storage, and particularly for applications in which the DESMODUR ®TT powder must be dispersed in viscous liquids, the tendency of the fine solid particles to compact and agglomerate may cause difficulties.

The problem arose, therefore, of improving the flowability of the finely divided dimerized 2,4-toluene diisocyanate and reducing the tendency of the solid to agglomerate. This problem has been solved by adding certain types of silica to the polyisocyanate.

SUMMARY OF THE INVENTION

The present invention thus relates to a process for improving the flowability and preventing the agglomeration of finely divided dimerized 2,4-toluene diisocyanate comprising adding precipitated silicas and/or pyrogenic silicas having a hydrophobic surface to said finely divided dimerized 2,4-toluene diisocyanate.

DETAILED DESCRIPTION OF THE INVENTION

The precipitated and/or pyrogenic silicas with hydrophobic surface are preferably added in quantities of from about 0.01 to about 10% by weight, most preferably in quantities from 0.1 to 2.5% by weight.

These silicas may be added at any stage in the process of preparing dimerized 2,4-toluene diisocyanate from its precursors. Precipitated and/or pyrogenic silicas with hydrophobic surface are preferably added to the reaction mixture after the solid dimerized 2,4-toluene diisocyanate is precipitated and before it is worked up and ground.

In another variation of the process, the silicas are added to the already dried and ground polyisocyanate and then vigorously mixed therewith.

Other additives may be used in addition to the precipitated and/or pyrogenic silicas with hydrophobic surface, such as $CaCO_3$, $BaSO_4$, talc, silicas having a hydrophilic surface, $Al_2O_3$, $Sb_2O_3$, and the like.

The invention further relates to finely divided, dimerized 2,4-toluene diisocyanate with improved flowability having a mean particle size of from about 2 to about 25 μm and contaning from about 0.01 to about 10% by weight of precipitated and/or pyrogenic silicas having a hydrophobic surface. The finely divided dimerized 2,4-toluene diisocyanate according to the invention is used as isocyanate component for the preparation of polymers containing urethane groups and/or urea groups.

Precipitated and pyrogenic silicas having a hydrophobic surface have long been known and available commercially. Examples include the products sold by Degussa AG under the names of AEROSIL ®R 202, AEROSIL ®R 805, AEROSIL ®R 812, AEROSIL ® R 972, AEROSIL ®R 974, AEROSIL ® R 976, SIPERNAT ® D10, and SIPERNAT ®D 17. Silicas with hydrophobic surfaces supplied by other manufacturers are also suitable.

These silicas may be added to the polyisocyanate after it has been worked up and dried, but they may also be added at any one or more stages in the preparation of dimerized 2,4-toluene diisocyanate, optionally subdivided into several portions. For example, the silicas may be added after precipitation, before isolation, before drying, before grinding, or after grinding of the solid substance. The silicas may also be added as suspensions in a suitable solvent.

Methods for the handling of silicas are described, for example, in the publication, "Schriftenreihe Pigmente, No. 28", available from Degussa AG.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Commercial finely ground, dimerized 2,4-toluene diisocyanate (particle size 2 to 25 m) (DESMODUR ®TT of Bayer AG) was used for carrying out the experiments.

Samples were prepared by successively introducing 100 parts by weight of DESMODUR ®TT, the given quantity of silica, and a further 100 parts by weight of DESMODUR ®TT into a new, unused 500 ml glass flask; closing the flask; and then shaking vigorously for one minute.

The following measurements were carried out on the resultant samples:

1. Powder cone test

A metal sieve was fixed 3 to 10 cm above a solid metal cylinder that was 50 mm in diameter and about 80 mm in height. The powder to be tested was poured onto the sieve and slowly pressed through the sieve by hand with the aid of a brush. The powder that dropped through the sieve collected as a cone on the metal cylinder and the height and angle of slope of the cone were measured. These data gave a direct measure of the free flowing property of the powder tested. A lower cone indicated that the powder was more free flowing than a higher cone.

2. Outflow test

Outflow vessels in the form of hour-glasses that have differing, specified outflow widths (13 mm, 12 mm, 9 mm, 8 mm, and 5 mm) and that have been rendered hydrophobic by means of a silicone emulsion were used for these measurements.

The powder to be tested was introduced into the measuring vessel while the outflow opening was kept closed. The outflow opening was then opened and the time required for the powder to flow out and the quantity of powder which flows out relative to the total quantity introduced into the vessel were measured.

The measurements were started using the measuring vessel having the greatest outflow width and were then carried out in vessels with progressively smaller outflow widths. The smaller outflow width at which powder was still able to flow out of the vessel indicated a more freeflowing powder. An outflow of "infinity" (designated by in the tables) indicates no flow or an insignificant flow rate.

EXAMPLE 1

A test series was carried out using an unmodified sample of DESMODUR® TT and several samples containing 1% by weight of different silicas having hydrophobic surface according to the invention. The samples were subjected to the powder cone test and the outflow test in vessels having an outflow width of 13 mm. The results obtained are shown in Table 1.

TABLE 1

| Additive | Height of cone (mm) | Funnel outflow Time (sec) | Funnel outflow Quantity (%) |
| --- | --- | --- | --- |
| None | 68 | ∞ | 0 |
| AEROSIL ® A 202[1] | 44 | 3 | 70 |
| AEROSIL ® A 805[1] | 43 | 1 | 100 |
| AEROSIL ® A 812[1] | 28 | 1 | 100 |
| AEROSIL ® A 972[1] | 41 | 1 | 100 |
| AEROSIL ® A 974[1] | 36 | 1 | 100 |
| SIPERNAT ® D 10[2] | 47 | 1 | 100 |

TABLE 1-continued

| Additive | Height of cone (mm) | Funnel outflow Time (sec) | Funnel outflow Quantity (%) |
| --- | --- | --- | --- |
| SIPERNAT ® D 17[2] | 34 | 1 | 100 |

∞ denotes "infinity".
[1]Trade Products of Degussa AG. For physical chemical data of the silicas, see "Schriftenreihe Pigmente, No. 23, Aerosil als Verdickungsmittel fur Flussigkeiten", Degussa AG.
[2]Trade Products of Degussa AG. For physical chemical data of the silicas, see "Fallungskieselsauren und Silikate, Herstellung, Eigenschaften und Anwendungen", Degussa AG.

The results clearly show that when the silicas according to the invention are used, the heights of the cones obtained are substantially less than those obtained with DESMODUR ® TT without silica and that outflow of the powder from the measuring vessel is only possible when silicas according to the invention are added.

EXAMPLE 2

Outflow tests were carried out as in Example 1 using the additives AEROSIL®A 812, AEROSIL®A 805, AEROSIL® A 974, and SIPERNAT® D 17 except that the outflow times and quantities were measured in measuring vessels with smaller outflow widths and the quantities of additives were varied. The results are shown in Table 2.

TABLE 2

| Additive | Quantity of additive (% by weight) | Funnel outflow Time (sec) Quantity (%) Size of funnel: | | | | |
| --- | --- | --- | --- | --- | --- | --- |
| | | 13 mm | 12 mm | 9 mm | 8 mm | 5 mm |
| AEROSIL ® R 812[1] | 0.25 | 3.0/80 | * | * | * | * |
| AEROSIL ® R 812[1] | 0.50 | 1.0/100 | 1.0/100 | 2.0/90 | * | * |
| AEROSIL ® R 812[1] | 1.00 | 1.0/100 | 1.0/100 | 1.5/100 | 1.5/100 | 5.0/90 |
| AEROSIL ® R 812[1] | 1.50 | 1.0/100 | 1.0/100 | 1.0/100 | 1.5/100 | 6.0/90 |
| AEROSIL ® R 812[1] | 2.00 | 1.0/100 | 1.0/100 | 1.0/100 | 2.0/100 | 4.0/90 |
| AEROSIL ® R 805[1] | 0.25 | 1.0/30 | * | * | * | * |
| AEROSIL ® R 805[1] | 0.50 | 1.0/80 | * | * | * | * |
| AEROSIL ® R 805[1] | 1.00 | 1.0/100 | 1.0/100 | 3.0/70 | * | * |
| AEROSIL ® R 805[1] | 1.50 | <1/100 | 1.0/100 | 2.5/100 | 3.0/90 | * |
| AEROSIL ® R 805[1] | 2.00 | <1/100 | <1/100 | 2.5/100 | 2.5/90 | * |
| AEROSIL ® R 974[1] | 0.25 | 1.5/50 | * | * | * | * |
| AEROSIL ® R 974[1] | 0.50 | 1.5/100 | 1.5/100 | 2.0/50 | * | * |
| AEROSIL ® R 974[1] | 1.00 | 1.0/100 | 1.0/100 | 3.0/100 | 2.5/100 | 5.0/80 |
| AEROSIL ® R 974[1] | 1.50 | 1.0/100 | 1.0/100 | 2.5/100 | 3.0/100 | 5.0/90 |
| AEROSIL ® R 974[1] | 2.00 | <1/100 | <1/100 | 2.5/100 | 2.5/100 | 5.0/90 |
| SIPERNAT ® D 17[2] | 0.25 | 1.5/70 | * | * | * | * |
| SIPERNAT ® D 17[2] | 0.50 | 1.5/100 | 1.5/100 | 2.0/100 | 3.0/100 | 4.5/80 |
| SIPERNAT ® D 17[2] | 1.00 | 1.0/100 | 1.5/100 | 2.0/100 | 3.0/100 | 4.5/80 |
| SIPERNAT ® D 17[2] | 1.50 | <1/100 | 1.0/100 | 2.0/100 | 2.5/100 | 4.0/90 |
| SIPERNAT ® D 17[2] | 2.00 | <1/100 | 1.0/100 | 2.0/100 | 2.5/100 | 4.0/90 |

* denotes ∞ sec/0% (where ∞ denotes "infinity")
[1]Trade Products of Degussa AG. For physical chemical data of the silicas, see "Schriftenreihe Pigmente, No. 23, Aerosil als Verdickungsmittel fur Flussigkeiten", Degussa AG.
[2]Trade Products of Degussa AG. For physical chemical data of the silicas, see "Fallungskieselsauren und Silikate, Herstellung, Eigenschaften und Anwendungen", Degussa AG.

The test results carried out with outflow vessels having smaller outflow widths confirm the results obtained in the Example 1 but, in addition, enabled the individual silicas to be more clearly differentiated in their positive effect on the flowability of DESMODUR ® TT.

EXAMPLE 3 (COMPARISON EXAMPLE)

Silicas not having a hydrophobic surface and other additives were used under the same conditions as in Example 1 for comparison. Table 3 shows that virtually no improvement in flowability is observed when these silicas were used.

TABLE 3

| Additive | Height of cone (mm) | Funnel outflow Time (sec) | Funnel outflow Quantity (%) |
|---|---|---|---|
| None | 68 | ∞ | 0 |
| AEROSIL ® 130[1] | 55 | 2 | 90 |
| AEROSIL ® 200[1] | 57 | ∞ | 0 |
| AEROSIL ® 380[1] | 57 | 4 | 80 |
| AEROSIL ® OX 50[1] | 61 | 3 | 70 |
| SIPERNAT ® 22[2] | 59 | 1 | 80 |
| SIPERNAT ® 22 LS[2] | 60 | 1 | 70 |
| SIPERNAT ® 44[2] | 58 | ∞ | 0 |
| FK 320[2] | 48 | 2 | 60 |
| FK 320 DS[2] | 47 | 1 | 80 |
| DUROSIL ®[2] | 51 | <1 | 50 |
| WESSALON S[2] | 54 | 1 | 70 |
| EXTRUSIL ®[2] | 57 | 1 | 80 |
| TRANSPAFILL[2] | 48 | 1 | 60 |
| VULKASIL ® S[3] | 60 | 1 | 30 |
| VULKASIL ® N[3] | 58 | 1 | 80 |
| Pure talc | 58 | 1 | 50 |
| Aluminum oxide C[4] | 54 | 1 | 70 |

[1]Trade Products of Degussa AG. For physical chemical data of the silicas, see "Schriftenreihe Pigmente, No. 23, Aerosil als Verdickungsmittel fur Flussigkeiten", Degussa AG.
[2]Trade Products of Degussa AG. For physical chemical data of the silicas, see "Fallungskieselsauren und Silikate, Herstellung, Eigenschaften und Anwendungen", Degussa AG.
[3]Trade products of Bayer AG. For physical chemical data, see "Anorganische Pigmente, Fullstoffe und Aktivatoren fur die Gummi-Industrie", Bayer AG.
[4]Trade products of Degussa AG. For physical chemical data, see "Schriftenreihe Pigmente, No. 13, Sythetische Kieselsauren als Hilfsmittel fur die Kunststoffindustrie".

What is claimed is:

1. A process for improving the flowability and preventing the agglomeration of finely divided dimerized 2,4-toluene diisocyanate comprising adding 0.01 to 10% by weight of a precipitated silica and/or pyrogenic silica having a hydrophobic surface to said finely divided dimerized 2,4-toluene diisocyanate.

2. A process according to claim 1 wherein 0.1 to 2.5% by weight of the precipitated silica and/or pyrogenic silica having a hydrophobic surface is added to said finely divided dimerized 2,4-toluene diisocyanate.

3. A process according to claim 1 wherein the finely divided dimerized 2,4-toluene diisocyanate has a mean particle size of from 2 to 25 μm.

4. A process according to claim 1 wherein the precipitated silica and/or pyrogenic silica having a hydrophobic surface is added during preparation of said dimerized 2,4-toluene diisocyanate.

5. A process according to claim 4 wherein the precipitated silica and/or pyrogenic silica having a hydrophobic surface is added after said dimerized 2,4-toluene diisocyanate is precipitated and before said dimerized 2,4-toluene diisocyanate is worked up and ground.

6. A process according to claim 1 wherein the precipitated silica and/or pyrogenic silica having a hydrophobic surface is added to the dimerized 2,4-toluene diisocyanate after said dimerized 2,4-toluene diisocyanate is dried and ground.

7. A process according to claim 1 additionally comprising adding an additive other than the precipitated silica and/or pyrogenic silica having a hydrophobic surface.

8. A process according to claim 7 wherein said additive is $CaCO_3$, $BaSO_4$, talc, a silica having a hydrophilic surface, $Al_2O_3$, or $Sb_2O_3$.

9. A finely divided dimerized 2,4-toluene diiscoyanate with improved flowability having a mean particle size of from 2 to 25 μm and containing from 0.01 to 10% by weight of a precipitated and/or pyrogenic silica having a hydrophobic surface.

10. In a process for preparing a polymer containing urethane groups and/or urea groups, the improvement wherein a finely divided dimerized 2,4-toluene diisocyanate prepared according to the process of claim 1 is used as the isocyanate component.

11. In a process for preparing a polymer containing urethane groups and/or urea groups, the improvement wherein a finely divided dimerized 2,4-toluene diisocyanate according to claim 9 is used as the isocyanate component.

* * * * *